United States Patent [19]

Fex et al.

[11] Patent Number: 4,778,789

[45] Date of Patent: Oct. 18, 1988

[54] PIPERAZINECARBOXAMIDES HAVING A PHENOXYALKYL OR THIOPHENOXYALKYL SIDE CHAIN

[75] Inventors: Tomas Fex, Lund; Knut G. Olsson, Malmö ; Aina L. Abramo, Järavallsvägen; Erik G. Christensson, Lund, all of Sweden

[73] Assignee: Aktiebolaget Leo, Sweden

[21] Appl. No.: 930,310

[22] PCT Filed: Jan. 31, 1986

[86] PCT No.: PCT/SE86/00038

§ 371 Date: Nov. 26, 1986

§ 102(e) Date: Nov. 26, 1986

[87] PCT Pub. No.: WO86/04584

PCT Pub. Date: Aug. 14, 1986

[30] Foreign Application Priority Data

Feb. 8, 1985 [SE] Sweden ............................ 8500573

[51] Int. Cl.$^4$ ................. A61K 31/495; C07D 241/04; C07D 295/00

[52] U.S. Cl. ................................... 514/210; 514/211; 514/212; 514/218; 514/255; 514/235.8; 540/484; 540/544; 540/575; 540/607; 540/609; 540/612; 544/107; 544/121; 544/357; 544/365; 544/372; 544/390; 544/391

[58] Field of Search ............... 544/357, 386, 390, 391, 544/398, 399, 401, 402, 403, 107, 121, 372, 365; 514/255, 461, 471, 619, 617, 622, 210, 212, 228, 232, 233, 238, 240, 211, 218; 540/544, 484, 112, 575, 607, 609

[56] References Cited

U.S. PATENT DOCUMENTS

| | | | |
|---|---|---|---|
| 3,000,892 | 9/1961 | Janssen ............................ | 544/390 |
| 3,962,249 | 6/1976 | Irikura . | |
| 4,219,551 | 8/1980 | Seidelmann et al. ............ | 514/255 |
| 4,413,006 | 11/1983 | Kanno et al. . | |

FOREIGN PATENT DOCUMENTS

| | | | |
|---|---|---|---|
| 42366A1 | 12/1981 | European Pat. Off. ............ | 544/390 |
| 80992A3 | 8/1983 | European Pat. Off. ............ | 544/390 |
| 2367067 | 5/1978 | France ............................ | 544/39 |
| WO85/00811 | 2/1985 | PCT Int'l Appl. ................ | 544/390 |
| 81008526 | 9/1983 | Sweden ............................ | 544/390 |
| 83009878 | 11/1983 | Sweden ............................ | 544/390 |
| 2037745 | 7/1980 | United Kingdom ............... | 544/390 |
| 2116967A | 10/1983 | United Kingdom ............... | 544/390 |
| 2163151A | 2/1986 | United Kingdom ............... | 544/390 |
| 2163152A | 2/1986 | United Kingdom ............... | 544/390 |
| 2163153A | 2/1986 | United Kingdom ............... | 544/390 |

OTHER PUBLICATIONS

Chemical Abstract, vol. 38, 6830b, 1962, "Hypoglycemic Agent".
Chemical Abstracts, vol. 102, 95674j; 1985, "Substituted Piperazin-1-yl-Acetic-Acid Amides and their Use".
Chemical Abstracts, 83, Abs. No. 131539u, (1975) p. 503.
Chemical Abstracts, 85, Abs. No. 33082m (1976) p. 407.

*Primary Examiner*—Richard L. Raymond
*Assistant Examiner*—Raymond Covington
*Attorney, Agent, or Firm*—Scully, Scott, Murphy & Presser

[57] ABSTRACT

Novel compounds of formula (I), wherein $R_1$ is selected from hydrogen, halogen; or trifluoromethyl; X is oxygen or sulfur; $R_2$ and $R_3$ are the same or different and selected from hydrogen or lower alkyl; m is 2 or 3; Y is oxygen or sulphur; Z is selected from: —$NR_4R_5$, formulae (II), (III) or (IV), wherein $R_4$ and $R_5$ are the same or different and selected from hydrogen, alkyl, cycloalkyl, cycloalkyl-alkyl, hydroxy-alkyl, alkoxyalkyl or alkanoyloxyalkyl, phenyl or phenyl-alkyl, wherein the phenyl groups may be unsubstituted or monosubstituted with halogen or $CF_3$; n is 0, 1, 2 or 3; $R_6$ and $R_7$ are the same or different and selected from hydrogen, lower alkyl, hydroxy, lower alkoxy or lower alkanoyloxy; p is 2 or 3; $R_8$ and $R_9$ are the same or different and selected from hydrogen or lower alkyl; $R_{10}$ is hydrogen, lower alkyl or lower alkanoyl. The new compounds can be used for treating mental disorders.

8 Claims, No Drawings

PIPERAZINECARBOXAMIDES HAVING A PHENOXYALKYL OR THIOPHENOXYALKYL SIDE CHAIN

BACKGROUND OF THE INVENTION

Drugs in use today for the treatment of mental disorders most often are associated with serious side effects. Antipsychotic drugs commonly cause disturbing extrapyramidal symptoms, and long term treatment may result in tardive dyskinesia. Antidepressants often exhibit cardiotoxicity, and anxiolytic drugs have addicting properties. As a result of these drawbacks efforts are being made to fine new pharmacologically active drugs which have fewer side effects.

The present invention relates to novel piperazine- and homopiperazinecarboxamides bearing a phenoxyalkyl or thiophenoxyalkyl side chain, which exhibit valuable pharmacological properties, and which have a low tendency to cause side effects.

Pharmacologically valuable piperazine carboxamides are previously known from British patent application No. 2,037,745. However, the compounds according to the British application differ from the compounds according to the present invention in being substituted in the 4-position with a very lipophilic 4,4-diphenylbutyl group. Furthermore, these previous compounds are very active in pharmacological models which may indicate potentation of noradrenaline and serotonine (e.g inhibition of muricide behaviour), which in turn may cause unwanted side effects, e.g. aneroxigenic. The compounds of the present invention are considerably less active in these pharmacological models indicating that fewer side effects are to be expected when compounds according to the present invention are used.

Piperazinecarboxamides substituted the 4-position with a butyrophenone side chain are known from Collect. Czech. Chem. Commun 1975, 40(4), 1218–30. The butyrophenone side chain is chemically distinctly different from a phenoxyalkyl or thiophenoxyalkyl group. Besides, the authors state that their compounds display CNS-activity only at high doses.

The French patent application 2367067 and the Swedish patent application 8100852-6 describe piperazine derivatives having a phenoxyalkyl side chain but in neither case are the compounds piperazinecarboxamides. The compounds according to the French patent application are chracterized by an analgesic effect that is not accompanied by any secondary effects (cf. the French application page 1, lines 20–24).

DESCRIPTION OF THE INVENTION

According to the invention there are provided novel compounds having the general formula:

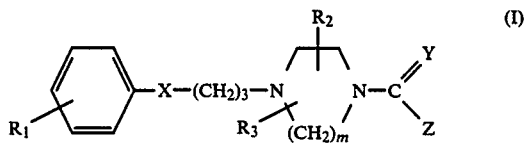
(I)

wherein $R_1$ is selected from hydrogen, halogen or trifluoromethyl;
X is oxygen or sulfur;
$R_2$ and $R_3$ are the same or different and selected from hydrogen or lower alkyl;
m is 2 or 3;
Y is oxygen or sulfur;
Z is selected from: $-NR_4R_5$ or

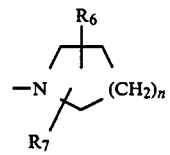

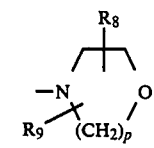

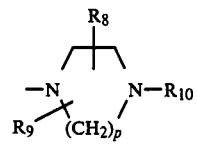

wherein $R_4$ and $R_5$ are the same or different and selected from hydrogen, alkyl, cycloalkyl, cycloalkyl-alkyl, hydroxy-alkyl, alkoxyalkyl, alkanoyloxyalkyl: phenyl or phenyl-alkyl, wherein the phenyl groups may be unsubstituted or monosubstituted with halogen or $CF_3$;
n is 0, 1, 2 or 3;
$R_6$ and $R_7$ are the same or different and selected from hydrogen, lower alkyl, hydroxy, lower alkoxy or lower alkanoyloxy;
p is 2 or 3;
$R_8$ and $R_9$ are the same or different and selected from hydrogen or lower alkyl;
$R_{10}$ is hydrogen, lower alkyl or lower alkanoyl, and the pharmaceutically active salts thereof,
and when used in the foregoing definitions the term alkyl is meant to include straight and branched, saturated and unsaturated hydrocarbon groups having 1 to 10 carbon atoms;
the term cycloalkyl is meant to include cyclic, saturated and unsaturated hydrocarbon groups having from 3 to 8 carbon atoms; the term alkoxy is meant to include straight and branched, saturated or unsaturated alkoxy groups having from 1 to 10 carbon atoms;
the term alkanoyloxy is meant to include straight and branched, saturated and unsaturated alkanoyloxy groups having from 1 to 10 carbon atoms;
the term lower is used when the groups mentioned above contain from 1 to 4 carbon atoms and
the term halogen is meant to include fluoro, chloro and bromo.

The compounds of formula (I) have basic properties and consequently they may be converted to their therapeutically active acid addition salts by treatment with appropriate acids; e.g. inorganic acids such as hydrochloric, hydrobromic, sulfuric, nitric and phosphoric acid, or organic acids such as acetic, propanoic, glycolic, lactic, malonic, oxalic, succinic, fumaric, tartaric, citric and pamoic acid.

Conversely, the salt form can be converted into the free base form by treatment with alkali.

In the compounds of the general formula (I) it is preferred that $R_1$ is halogen or $CF_3$ and that $R_1$ is situated in the m- or p-position.

If selected from halogen it is preferred that $R_1$ is F or Cl, especially F.

When $R_1$ is $CF_3$ it is preferably situated in the m-position.

It is preferred that X is oxygen, and that $R_2$ and $R_3$ are hydrogen.

When $R_2$ and $R_3$ are lower alkyl, methyl and ethyl are preferred, especially methyl.

It is preferred that $m=2$.

It is preferred that Y is oxygen.

When Z is $NR_4R_5$ those compounds are preferred wherein $R_4$ and $R_5$ together contain less than ten carbon atoms.

Also, as regard the substituents $R_4$ and $R_5$ those compounds are preferred wherein $R_4$ and $R_5$ are selected from hydrogen, alkyl, cycloalkyl, cycloalkyl-alkyl and hydroxyalkyl, especially alkyl and cycloalkyl.

As regards the substituents $R_6$ and $R_7$ it is preferred that one of them is hydrogen and the other hydrogen or lower alkyl.

As regards the substituents $R_8$ and $R_9$ those compounds are preferred wherein both of them are hydrogen.

When Z is a heterocyclic ring containing two heteroatoms, it is preferred that one of the heteroatoms is oxygen.

Also as regards Z it is preferred that Z does not contain any asymmetric carbon atoms.

The following compounds are preferred:
4-/3-(p-fluorophenoxy)propyl/-N-methyl-1-piperazinecarboxamide
4-/3-(p-fluorophenoxy)propyl/-N-ethyl-1-piperazinecarboxamide
4-/3-(p-fluorophenoxy)propyl/-N-cyclopropyl-1-piperazinecarboxamide
4-/3-(m-trifluoromethyl-phenoxy)propyl/-N-ethyl-1-piperazinecarboxamide
4-/3-(p-fluorophenoxy)propyl/-N-methyl-1-piperazinethiocarboxamide
4-/3-(p-fluorothiophenoxy)propyl/-N-methyl-1-piperazinecarboxamide
4-/3-(p-fluorothiophenoxy)propyl/-N-ethyl-1-piperazinecarboxamide
4-/3-(p-fluorothiophenoxy)propyl/-N-cyclopropyl-1-piperazinecarboxamide
4-/3-(p-fluorothiophenoxy)propyl/-N-methyl-1-piperazinethiocarboxamide
4-/3-(p-fluorophenoxy)propyl/-N,N-dimethyl-piperazinecarboxamide
1-morpholinocarbonyl-4-/3-(p-fluorophenoxy)propyl/-piperazine Compounds wherein one or both of $R_2$ and $R_3$ are alkyl are racemic mixtures, and these may consequently be resolved into enantiomers.

The compounds of formula (I) and their pharmaceutically acceptable salts have valuable pharmacological properties making them useful for treatment of mental disorders such as psychoses, depression and anxiety. For example they may be useful for the prophylaxis and/or treatment of schizophrenia, mania or senile, involutional or organic psychoses as well as depressive psychoses, depression and anxiety.

Psychosomatic disorders caused by anxiety and stress should be alleviated by compounds of formula (I).

The new compounds may also be used in the prophylaxis and treatment of aggressive behaviour, which may be associated with mentally retarded and/or behaviourally disturbed patients and other form of aggression of either known or unknown etiology.

The new compounds may be useful in the treatment of aggressive behaviour in animals, especially in pigs, and also in promoting the development of a natural hierarchy in groups of animals without bursts of aggression and in calming of anxious and stressed animals.

The compounds of formula (I) have a clear limbic profile of action and are thus not likely to cause extrapyramidal side effects. This is evidenced by their ability to inhibit amphetamine induced locomotion in mice, whereas they do not block amphetamine induced stereotypies. Their ability to inhibit isolation induced aggression in male mice is also the result of activity in limbic brain areas. Extrapyramidale side effects are highly undesirable and are commonly seen with antipsychotics in clinical use today.

Effective quantities of any of the foregoing pharmacologically active compounds of formula (I) may be administered to a human being or an animal for therapeutic purposes according to usual routes of administration and in usual forms, such as orally in solutions, emulsions, suspensions, pills tablets and capsules, in pharmaceutically acceptable carriers and parenterally in the form of sterile solutions. For the parenteral administration of the active substance the carrier of excipient may be a sterile, parenterally acceptable liquid, e.g. water, or a parenterally acceptable oil, e.g. arachidic oil.

The compounds of formula (I) may if desired be administered in various slow release formulations.

Although very small quantities of the active materials of the present invention are effective when minor therapy is involved or in the cases of administration to subjects having a relatively low body weight, unit dosages are usually from 2 milligrams upwards, preferably 25, 50 or 100 milligrams or even higher depending on the condition to be treated and the age and weight of the patients as well as the response to the medication.

The unit dose may be from 0.1 to 200 milligrams, preferably from 10 to 50 milligrams. Daily dosages should preferably range from 10 milligrams to 400 milligrams. The exact individual dosages as well as daily dosages will, of course, be determined according to standard medical principles under the direction of a physician or veterinarian.

METHODS OF PREPARATION

The compounds having the general formula (I) may be prepared by conventional methods.

Method 1

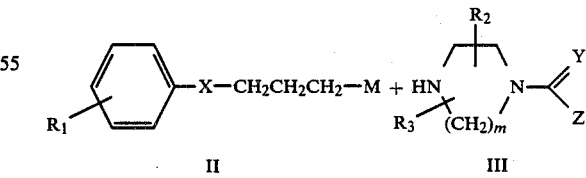

II   III

A compound of formula II, wherein $R_1$ and X are as defined above, and wherein M is a suitable leaving group such as halogen and alkyl- or arylsulfonate is reacted with a compound of formula (III) wherein $R_2$, $R_3$, Y, Z and m are as defined previously. The reactions may be carried out using standard N-alkylating procedures.

Method 2

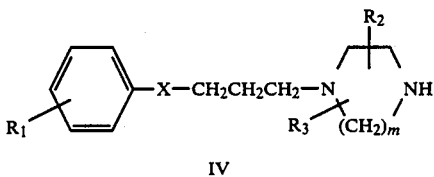

IV

R₄—NCO  (V)

R₄—NCS  (VI)

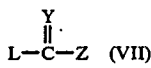

L—C—Z  (VII)

A compound of formula (IV), wherein $R_1$, X, $R_2$, $R_3$ and m are as defined above, is reacted with an isocyanate of formula (V) or an isothiocyanate of formula (VI) or a carbamoyl derivative of formula (VII), wherein $R_4$, Y and Z are as previously defined, and wherein L is a suitable leaving group such as halogen, phenoxy and substituted phenoxy (e.g. p-nitrophenoxy). The reactions may be carried out using standard procedures. The addition of an appropriate base may in some instances facilitate the reaction, and may if acid is formed during the reaction serve to neutralize this.

Method 3

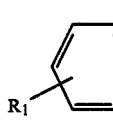 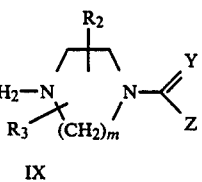

VIII    IX

A compound of formula (VIII) wherein $R_1$ and X are as previously defined is reacted with a compound of formula (IX) wherein M, $R_2$, $R_3$, m, Y and Z are as defined previously. The reaction is carried out using standard phenolate or thiophenolate alkylating conditions.

Method 4

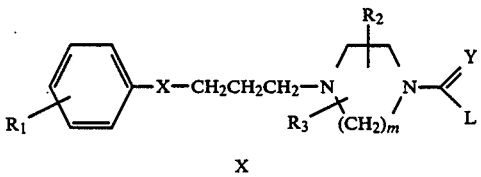

X

A compound of formula (X) wherein $R_1$, X, $R_2$, $R_3$, m, Y and L are as defined above is reacted with a compound of formula Z—H wherein Z is as previously defined. The reaction is carried out using standard procedures. When L is a poor leaving group and/or when Z—H is a poor nucleophile it may be advantageous to use a large excess of Z—H and/or to heat the reaction mixture for a longer period of time.

The intermediate X may be prepared by standard procedures according to:

Method 5

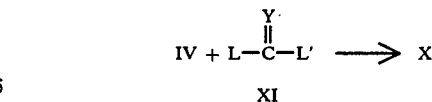

A compound of formula IV is reacted with a compound of formula XI wherein L and Y are as previously defined, and L' is a suitable leaving group such as halogen, phenoxy and substituted phenoxy (e.g. p-nitrophenoxy). Most commonly at least one of L and L' is halogen. The reaction is preferably performed in an inert solvent, and an appropriate base may be added to take care of the acid formed during the reaction.

The intermediate IV may be prepared by conventional methods according to:

Method 6

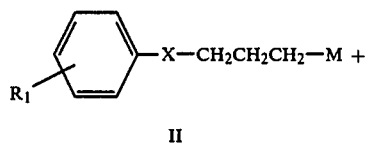

II

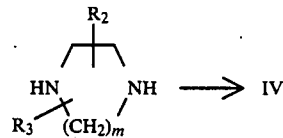

A compound of formula II is reacted with an excess of amine, wherein $R_2$ and $R_3$ are as defined above, using standard N-alkylating conditions.

EXAMPLES

The following examples are intended to illustrate but not to limit the scope of the invention, although the compounds named are of particular interest for our intended purposes. These compounds have been designated by a number code, a:b, where "a" means the number of the example wherein the preparation of the compound in question is described, and "b" refers to the order of the compounds prepared according to that example. Thus, compound 1:2 means the second compound prepared according to Example 1.

The structures of the compounds are confirmed by NMR, mass spectra and elementary analysis. When melting points are given, these are uncorrected.

Example 1

3.6 g (0.015 mole) of 1-/3-(p-fluorophenoxy)propyl/-piperazine was dissolved in 20 ml of toluen and cooled in an ice bath. 0.9 g (0.015 mole) of methylisocyanate dissolved in 35 ml of toluene was added dropwise during 15 minutes. The reaction mixture was allowed to reach room temperature and the solvent was subsequently removed by evaporation. The residue was recrystallized from toluene/ligroin to yield 4.2 g of 4-/3-(p-fluorophenoxy)propyl/-N-methyl-1-piperazinecarboxamide (1:1), M.p. 122°–23° C.

The corresponding hydrochloride (1:2) was prepared by dissolving 4.0 g of the base in ether/abs.ethanol and adding and excess of HCl in ethanol. The hydrochloride which precipitated was recrystallized from abs.ethanol. Yield 3.6 g, m.p. 222°–24° C.

Using essentially the same procedure the following compounds are prepared (isolated as the free bases or as the corresponding salts) from the corresponding starting materials.

1:3 4-/3-(p-fluorophenoxy)proyl/-N-ethyl-1-piperazinecarboxamide hydrochloride, m.p. 211°–12° C.

1:4 4-/3-(p-fluorophenoxy)propyl/-N-cyclopropyl-1-piperazinecarboxamide hydrochloride, m.p. 217°–18° C.

1:5 4-/3-(p-fluorophenoxy)propyl/-N-(1-methylethyl)-1-piperazinecarboxamide

1:6 4-/3-(p-fluorophenoxy)propyl/-N-hexyl-1-piperazinecarboxamide

1:7 4-/3-(p-fluorophenoxy)propyl/-N-cyclohexyl-1-piperazinecarboxamide

1:8 4-/3-(p-fluorophenoxy)propyl/-N-(2-propenyl)-1-piperazinecarboxamide

1:9 4-/3-(p-chlorophenoxy)propyl/-N-ethyl-1-piperazinecarboxamide

1:10 4-/3-(m-trifluoromethyl-phenoxy)propyl/-N-ethyl-1-piperazinecarboxamide hydrochloride, m.p. 196°–98° C.

1:11 4-(3-phenoxypropyl)-N-ethyl-1-piperazinecarboxamide

1:12 4-/3-(p-fluorophenoxy)propyl/-N-methyl-1-piperazinethiocarboxamide hydrochloride, m.p. 182°–83° C.

1:13 4-/3-(p-fluorothiophenoxy)propyl/-N-ethyl-1-piperazinecarboxamide hydrochloride, m.p. 195°–7° C.

1:14 4-/3-(p-fluorothiophenoxy)propyl/-N-cyclopropyl-1-piperazinecarboxamide

1:15 4-/3-(p-fluorothiophenoxy)propyl/-N-methyl-1-piperazinethiocarboxamide

1:16 4-/3-(p-fluorophenoxy)propyl/-2,5-trans-dimethyl-N-ethyl-1-piperazinecarboxamide 1:17 4-/3-(p-fluorophenoxy)propyl/-2,5-trans-dimethyl-N-cyclopropyl-1-piperazinecarboxamide 1:18 4-(3-phenoxypropyl)-2,5-trans-dimethyl-N-(1-methylethyl)-1-piperazinecarboxamide hydrochloride, m.p. 185°–6° C.

1:19 4-/3-(p-fluorophenoxy)propyl/-N-ethyl-1-(1,4-diazacycloheptanecarboxamide)

1:20 4-/3-(p-fluorophenoxy)propyl/-N-cyclohexyl-1-(1,4-diazacycloheptanecarboxamide)hydrochloride, m.p. 221°–4° C. (dec.).

1:21 4-/3-(p-fluorothiophenoxy)propyl/-N-ethyl-1-(1,4-diazacycloheptanecarboxamide)

1:22 4-/3-(p-fluorophenoxy)propyl/-N-phenyl-1-piperazinecarboxamide, hydrochloride, m.p. 202°–3° C.

1:23 4-/3-(p-fluorophenoxy)propyl/-N-p-chlorophenyl-1-piperazinecarboxamide

1:24 4-/3-(p-fluorophenoxy)propyl/-N-phenylmethyl-1-piperazinecarboxamide

Example 2

7.0 g (0.03 mol) of 1-/3-(p-fluorophenoxy)propyl/-piperazine was dissolved in 45 ml of conc. acetic acid. 3.2 g (0.04 mol) KOCN was dissolved in 20 ml of H$_2$O and added to the reaction mixture which subsequently was stirred (for) 20 h. at RT. After cooling to 0° C. the reaction mixture was made basic by addition of 5N NaOH. The product separated slowly by crystallization and was filtered off. It was dissolved in CH$_2$Cl$_2$ and the solution was washed with H$_2$O, dried with Na$_2$SO$_4$, and the solvents evaporated. The residual oil crystallized and was recrystallized from toluene/ligroin to yield 5.9 g of 4-/3-(p-fluorophenoxy)propyl/-1-piperazine carboxamide (2:1), m.p. 98°–100° C.

The corresponding hydrochloride was prepared by dissolving 5.5 g of the base in 50 ml of a mixture of abs. ethanol/ether. Addition of an excess of HCl in ethanol and additional ether precipitated the hydrochloride. After recrystallization from isopropanol 4.7 g of the hydrochloride (2:2) was obtained, m.p. 209°–10° C.

Using essentially the same procedure (heating of the reaction mixture is required) the following compound is prepared from the corresponding starting materials:

2:3 4-/3-(p-fluorophenoxy)propyl/-1-piperazinethiocarboxamide

Example 3

12.5 g (0.031 mol) of p-nitrophenyl-4-/3-(p-fluorophenoxy)propyl/-1-piperazine carboxylate was stirred in a mixture of 20 ml of dimethylamine and 20 ml of THF at 0° C. for 3 days. The reaction mixture was partitioned between ether and H$_2$O. The ether phase was washed twice with a Na$_2$CO$_3$ solution and twice with a NaCl-solution. The mixture was dried with Na$_2$SO$_4$. After filtration excess of HCl in ethanol was added to precipitate the hydrochloride. After filtration and recrystallization from ethyl acetate/ethanol was obtained 5.5 g of 4-/3-(p-fluorophenoxy)propyl/-N,N-dimethyl-1-piperazinecarboxamide, hydrochloride (3:1), m.p. 185°–7° C.

Using essentially the same procedure (sometimes omitting the cosolvent THF and heating in the case of more unreactive amines) the following compounds were prepared (isolated as the free bases or as the corresponding salts) from the corresponding starting materials.

3:2 1-morpholinocarbonyl-4-/3-(p-fluorophenoxy)-propyl/-piperazine, hydrochloride, m.p. 192°–3° C.

3:3 1-pyrrolidinocarbonyl-4-/3-(p-fluorophenoxy)-propyl/-piperazine

3:4 1-piperidinocarbonyl-4-/3-(p-fluorophenoxy)-propyl/-piperazine

3:5 1-(4-methylpiperidinocarbonyl)-4-/3-(p-fluorophenoxy)propyl/-piperazine, hydrochloride, m.p. 216°–17° C.

3:6 1-(4-hydroxy-piperidinocarbonyl)-4-/3(p-fluorophenoxy)propyl/-piperazine

3:7 1-(4-methyl-piperazinocarbonyl)-4-/3-(p-fluorophenoxy)propyl/-piperazine

3:8 1-(4-acetyl-piperazinocarbonyl)-4-/3-(p-fluorophenoxy)propyl/-piperazine

3:9 4-/3-(p-fluorophenoxy)propyl/-N-(2-hydroxyethyl)-1-piperazinecarboxamide, hydrochloride, m.p. 186°–7° C.

Example 4

25 g (0.105 mol) of 1-/3-(p-fluorophenoxy)propyl/-piperazine was dissolved in 300 ml of toluene, 20 ml of triethylamine was added and the mixture was cooled to 0° C. 21.2 g (0.105 mol) of p-nitrophenyl-chloroformate in 300 ml of toluene was added dropwise. The reaction mixture was stirred at RT for 3 h. The triethylamine hydrochloride was filtered off and the solvents were evaporated. The residue was dissolved in methanol and the product was allowed to crystallize overnight. The product was filtered off to yield 25 g of p-nitrophenyl-4-/3-(p-fluorophenoxy)propyl/-1-piperazine-carboxylate (4:1), m.p. 101°–02° C.

Example 5

82 g (0.43 mol) of 1-chloro-3-(p-fluorophenoxy)-propane and 262 g of piperazine were dissolved in 700 ml of isopropanol and refluxed for 16 h. The reaction mixture was allowed to reach RT and piperazine which had precipitated was filtered off. The solvents were evaporated and the residue was dissolved in $CH_2Cl_2$. After washing with sat. NaCl-solution and drying with $Na_2SO_4$ the $CH_2Cl_2$ was evaporated and the residue destilled to yield 75 g of 1-/3-(p-fluorophenoxy)propyl/-piperazine (5:1), b.p. 104°–6° C. (0.05 mm Hg).

Example 6

This example illustrates the potency of compounds of formula (I) and their pharmaceutically active acid addition salt for treatment of mental disorders.

Test: Isolation induced aggressive behaviour test

Male mice subjected to prolonged isolation develop aggressive behaviour against each other when paired (Yen, C. Y. et al., Arch. Int. Pharmacodyn. 123, 179, (1959): Valzelli, L., Adv. Pharmacol. 5, 79 (1967). All clinically used neuroleptics and antidepressants studied in this test inhibit this aggressive behaviour although their activity may differ. Also anxiolytic drugs, e.g. diazepam, are active on this kind of aggressive behaviour. The clinical correlation of this test indicates tranquillizing and anxiolytic activities as well as antiaggressive properties as such (Duncan, R. L. et al., J. Med. Chem. 13, 1 (1970)).

This type of aggression is interesting because it is known that this kind of emotional behaviour might be located in limbic structures in the brain (MacLean, P. D., Psychosom. Med. 11, 338 (1949)).

Every week male NMRI mice, weighing 20–22 g, were isolated in Makrolon cages for three weeks with diet and water ad libitum. A piece of cardboard was placed between the cages to prevent visual contact.

To test aggressiveness the mice were paired in a neutral area, a beaker (14 cm high and diameter 14 cm). A pair is considered aggressive if both the animals show clear signs of fighting within 5 minutes. This fighting is characterized by biting and vocalization. A soon as fighting is seen, the mice are separated and brought to their home cage (every second mouse is marked). If only one of two mice exhibit aggressive behaviour the aggressive one is paired with another to make a well matched, aggressive pair. Animals showing no aggression are discarded.

The frequency of paired mice exhibiting fighting varies from 50–100 percent depending on the time of the year. The test substance is administered s.c. (0.2–0.4 ml/20 g). The mice are paired 0.5 hour after the injection for trials of 5 minutes' duration.

The $ED_{50}$-value (mg/kg) reported is the dose inhibiting aggressive behaviour among 50 percent of the pairs 0.5 hour after drug administration.

TABLE

Isolation induced aggressive behaviour test

| Compound | $ED_{50}$ mg/kg s.c. |
|---|---|
| 1:3 | 5 |
| Thioridazine[a] | 5 |
| Diazepam[b] | 6.7 |

[a]Merck Index, 10th Ed., 9202
[b]Merck Index, 10th Ed., 2967

Example 7

The following formulations are representative for all of the pharmacologically active compounds of this invention. Example of a suitable capsule formulation:

|  | Per capsule, mg |
|---|---|
| Active ingredient, as salt | 10 |
| Lactose | 250 |
| Starch | 120 |
| Magnesium stearate | 5 |
| Total | 385 |

In case of higher amounts of active ingredient, the amount of lactose used may be reduced.

Example of a suitable tablet-formulation:

|  | Per tablet, mg |
|---|---|
| Active ingredient, as salt | 10 |
| Potato starch | 90 |
| Colloidal silica | 10 |
| Talc | 20 |
| Magnesium stearate | 2 |
| 5% aqueous solution of gelatin | 25 |
| Total | 157 |

Solutions for parenteral applications by injection can be prepared in an aqueous solution of a water-soluble pharmaceutically acceptable salt of the active substance preferably in a concentration of from about 0.5% to about 5% by weight. These solutions may also contain stabilizing agents and/or buffering agents and may conveniently be provided in various dosage unit ampoules.

The pharmaceutical preparations may also contain therapeutically useful substances other than the pharmacologically active compounds of formula (I).

We claim:

1. Novel compounds having the general formula:

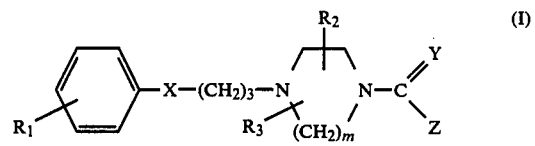

(I)

wherein $R_1$ is selected from hydrogen, halogen or trifluoromethyl;
X is oxygen or sulfur;
$R_2$ and $R_3$ are the same or different and selected from hydrogen or lower alkyl;
m is 2 or 3;
Y is oxygen or sulfur;
Z is selected from:
—$NR_4R_5$ or

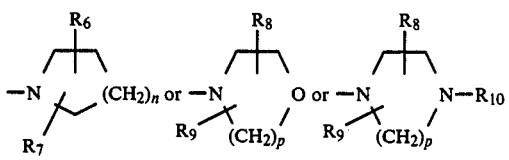

wherein $R_4$ and $R_5$ are the same or different and selected from hydrogen, alkyl, cycloalkyl, cycloalkyl-alkyl, hydroxy-alkyl, alkoxyalkyl or alkanoyloxyalkyl, phenyl or phenyl-alkyl, wherein the phenyl groups may be unsubstituted or monosubstituted with halogen or $CF_3$;

n is 0, 1, 2 or 3;

$R_6$ and $R_7$ are the same or different and selected from hydrogen, lower alkyl, hydroxy, lower alkoxy or lower alkanoyloxy;

p is 2 or 3;

$R_8$ and $R_9$ are the same or different and selected from hydrogen or lower alkyl;

$R_{10}$ is hydrogen, lower alkyl or lower alkanoyl, wherein the term alkyl is meant to include straight and branched, saturated and unsaturated hydrocarbon groups having 1 to 10 carbons;

the term cycloalkyl is meant to include cyclic, saturated and unsaturated hydrocarbon groups having 3 to 8 carbons;

the term alkoxy is meant to include straight and branched, saturated or unsaturated alkoxy groups and the term alkanoyloxy is meant to include straight and branched, saturated and unsaturated alkanoyloxy groups both having 1 to 10 carbons and the pharmaceutically active salts thereof.

2. A compound according to claim 1 characterized in that Z is selected from the group consisting of
—$NR_4R_5$ or

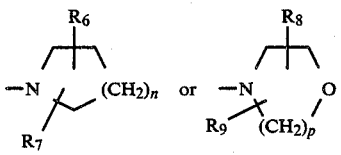

$R_4$ and $R_5$ are selected from the group consisting of hydrogen, alkyl, cycloalkyl, cycloalkyl-alkyl and hydroxy-alkyl;

one of $R_6$ and $R_7$ is hydrogen and the other is hydrogen or lower alkyl;

and that $R_8$ and $R_9$ are hydrogen.

3. A compound according to claim 1 or 2 characterized in that $R_2$ and $R_3$ are hydrogen.

4. A compound according to any of the claims 1 or 2 characterized in that m=2.

5. A compound according to any of the claims 1 or 2 characterized in that X and Y are oxygen.

6. A compound according to claim 1 or 2 characterized in that $R_1$ is F.

7. A compound according to claim 1 selected from the following group:
4-/3-(p-fluorophenoxy)propyl/-N-methyl-1-piperazinecarboxamide
4-/3-(p-fluorophenoxy)propyl/-N-ethyl-1-piperazinecarboxamide
4-/3-(p-fluorophenoxy)propyl/-N-cyclopropyl-1-piperazinecarboxamide
4-/3-(m-trifluoromethyl-phenoxy)propyl/-N-ethyl-1-piperazinecarboxamide
4-/3-(p-fluorophenoxy)propyl/-N-methyl-1-piperazinethiocarboxamide
4-/3-(p-fluorothiophenoxy)propyl/-N-methyl-1-piperazinecarboxamide
4-/3-(p-fluorothiophenoxy)propyl/-N-ethyl-1-piperazinecarboxamide
4-/3-(p-fluorothiophenoxy)propyl/-N-cyclopropyl-1-piperazinecarboxamide
4-/3-(p-fluorothiophenoxy)propyl/-N-methyl-1-piperazinethiocarboxamide
4-/3-(p-fluorophenoxy)propyl/-N,N-dimethyl-1-piperazinecarboxamide
1-morpholinocarbonyl-4-/3-(p-fluorophenoxy)-propyl/-piperazine.

8. Pharmaceutical compositions containing as an active ingredient one or more of the compounds having the general formula (I), preferably together with a pharmaceutically acceptable carrier and, if desired, other pharmacologically active agents.

* * * * *